United States Patent [19]

Usui et al.

[11] 4,356,258

[45] Oct. 26, 1982

[54] SILVER HALIDE COLOR PHOTOGRAPHIC MATERIAL CONTAINING YELLOW COUPLER

[75] Inventors: Tugumoto Usui; Katsunori Kato, both of Hachioji; Tamotsu Kojima, all of Kokubunji, Japan

[73] Assignee: Konishiroku Photo Industry Co., Ltd., Japan

[21] Appl. No.: 209,030

[22] Filed: Nov. 21, 1980

[30] Foreign Application Priority Data

Nov. 21, 1979 [JP] Japan ................................. 54/151482

[51] Int. Cl.$^3$ ................................................ G03C 1/40
[52] U.S. Cl. .................................... 430/557; 430/558; 430/389
[58] Field of Search ................ 430/556, 557, 472, 475, 430/388, 389, 558

[56] References Cited

U.S. PATENT DOCUMENTS

| | | | |
|---|---|---|---|
| 2,298,443 | 10/1942 | Weissberger | 430/556 |
| 2,350,138 | 5/1944 | Weissberger | 430/556 |
| 3,408,194 | 10/1968 | Loria | 430/556 |
| 4,133,958 | 1/1979 | Boie et al. | 430/557 |
| 4,264,721 | 4/1981 | Shimano et al. | 430/557 |
| 4,289,847 | 9/1981 | Ishikawa et al. | 430/557 |

*Primary Examiner*—J. Travis Brown
*Attorney, Agent, or Firm*—Finnegan, Henderson, Farabow, Garrett & Dunner

[57] ABSTRACT

A photographic acylacetanilide yellow coupler having at the acyl or anilide portion thereof a moiety represented by —X—Y—Z where X represents —NHCO— or —CONH— radical, Y represents a divalent organic radical, Z represents

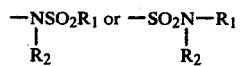

wherein $R_1$ is an alkyl or aryl radical, and a color photographic material containing an acylacetanilide yellow coupler.

1 Claim, No Drawings

SILVER HALIDE COLOR PHOTOGRAPHIC MATERIAL CONTAINING YELLOW COUPLER

The present invention relates to a yellow coupler and a silver halide color photosensitive material.

In the color development process, with the movement in recent years of silver halide photosensitive materials to color ones, the processing amount of color photographic materials has become increased, giving rise to a question of how to speed up the processing.

In order to speed up processing some endeavors have been made to raise the color developing efficiency by adding benzyl alcohols to the developing solution to improve the permeability of the developing agent.

However, as for the addition of benzyl alcohols, the reduction of the adding amount or the removal of the chemical is called for because of the problem of environmental pollution, e.g., for the increase in BOD (biochemical oxygen demand).

On the other hand, couplers to be incorporated into emulsion layers; i.e., couplers in emulsion, are provided with radicals for settling the couplers so as not to diffuse across the emulsion layers. These radicals are called "diffusion preventive radicals". Yellow couplers having alkylamide type diffusion preventive radicals among these diffusion preventive radicals, particularly, aryloxyalkylamide type diffusion preventive radicals such as described in British Pat. Nos. 1,040,710 and 1,077,874, U.S. Pat. No. 3,408,194, Japanese L-O-P Publication Nos. 48-29432, 48-66834, 49-1229, 49-10736, 50-28834 and 47-26133 are preferable in solubility and dispersibility, and photographic characteristics such as the spectral absorption characteristics (maximum absorption wavelength is on the longer wavelength side) of the resulting dyes and their image preservability are also excellent, thus being extensively used in the photographic industry, today. However, it is known that the couplers mentioned above, if the benzyl alcohol contained is reduced or removed therefrom, become worse in the reactivity with the oxidized product of developing agents; i.e., the color developing efficiency.

On the other hand, other couplers having sulfonamide type and sulfamoyl type diffusion preventive radicals at the anilide portion of yellow couplers, such as described in U.S. Pat. Nos. 2,298,443 and 2,350,138, British Pat. Nos. 1,187,860 and 1,160,628, West German Pat. Nos. 2,454,641 and 2,503,079, Japanese Pat. No. 48-15873, Japanese L-O-P Publications Nos. 49-88518, 50-87650 and 52-115219, etc. are known to be preferable in the color development efficiency and also well known to be more excellent than alkylamide type yellow couplers in that even when benzyl alcohol is removed or reduced the color development characteristics are not deteriorated.

However, sulfonamide type yellow couplers and sulfamoyl type yellow couplers, since their maximum absorption wavelength shifts toward longer wavelength side, have tendency to increase in the absorption of magenta region which is undesirable for yellow couplers. Further, sulfonamide type yellow couplers have such drawbacks that not only does their dispersibility becomes worse but their image preservability becomes deteriorated.

Therefore, an object of the present invention is to provide a silver halide color photosensitive material improved in the image preservability as well as spectral absorption characteristics, which yields a dye image having sufficient densities even when processed in a color photographic developer containing no benzyl alcohol or reduced amount of benzyl alcohol.

The object of the present invention is attainable by incorporating into the coupler of the present invention an acylacetamide type yellow coupler having at its acyl portion or anilide portion a radical having formula [I].

$$-X-Y-Z \quad [I]$$

wherein X is —NHCO— or —CONH—, Y is a divalent organic radical, Z is

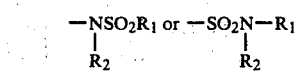

wherein $R_1$ is a substituted or non-substituted alkyl or aryl group, $R_2$ is a hydrogen atom or a substituted or nonsubstituted alkyl or aryl group.

In Formula I, the group represented by Y may be whatever divalent organic group combinable with both X and Z, but preferably be a group such that at least one of such radicals are combined as substituted or nonsubstituted alkylene groups, e.g., methylene, ethylene, propylene, butylene; arylene radicals, e.g., phenylene, naphthylene; alkenylene radicals, e.g., vinylene, butenylene; and a group of two or more radicals combined such that any one of oxy, thio and amino radicals is combined with any one of the above radicals, such as, phenyleneoxyalkylene, phenylenethioalkylene.

The substituted alkyl radicals or the substituents of the aryl radicals represented by the foregoing $R_1$ or $R_2$ include alkyl radicals such as methyl, ethyl or dodecyl; aryl radicals such as phenyl; aralkyl radicals such as benzyl; and the groups substitutable with Y include halogen such as chlorine or fluorine; alkyl radicals such as methyl, propyl or dodecyl; aryl radicals such as phenyl or naphthyl; amino radicals such as alkylamino, arylamino or acylamide; carboxyl radicals; alkoxylcarbonyl radicals such as methoxycarbonyl, butoxycarbonyl or dodecylcarbonyl; aryloxycarbonyl radicals such as phenoxycarbonyl; carbamoyl radicals such as dodecylcarbamoyl or phenylcarbamoyl; sulfamoyl radicals such as octylsulfamoyl, dodecylsulfamoyl or phenylsulfamoyl; alkylthio radicals such as dodecylthio; arylthio radicals such as phenylthio; alkylsulfonyl radicals such as dodecylsulfonyl; arylsulfonyl radicals such as phenylsulfonyl; hydroxyl radical; cyano radical; nitro radical, etc., and the foregoing substituted alkyl and aryl radicals may be further substituted with the any groups substitutable with Y.

The couplers of the present invention are characterized in having a radical represented by Formula I at the acyl portion or anilide portion of acylacetanilide type yellow couplers, and in the couplers of the present invention the residue of the coupler from which the radical represented by Formula I is removed are acylacetanilide type yellow couplers, but preferred coupler residues are of Formula II

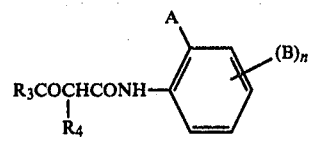

wherein $R_3$ or phenyl group contains a moiety represented by the Formula I, $R_3$ represents a substituted or nonsubstituted alkyl or aryl radical, preferably, a branched chain alkyl radical or a phenyl radical, most preferably, a tert-butyl radical. Substituents thereof are not limited thereto but include halogen atom such as chlorine, fluorine; alkyl radicals such as methyl, ethyl, t-butyl; aryl radicals such as phenyl, naphthyl; alkoxy radicals such as methoxy, ethoxy, t-butoxy; aryloxy radicals such as phenoxy; alkylthio radicals such as ethylthio, hexylthio; arylthio radicals such as phenylthio; acyl radicals such as acetyl, pivaloyl, benzoyl, methylsulfonyl, phenylsulfonyl; etc. A represents a halogen atom, alkoxy or aryloxy, preferably, a halogen atom, particularly chlorine, or a lower alkyl radical having 1–4 carbon atoms, particularly methoxy, while B represents one of radicals substitutable with benzene, e.g., halogen atoms such as fluorine, chlorine; alkyl radicals such as methyl, ethyl, methoxymethyl; alkoxy radicals such as methoxy, butoxy; aryloxy radicals such as benzoyloxy; all of which radicals may have substituents respectively, the substituents being the same as those in the case of $R_3$. n is 0 or 1.

$R_4$ may be whatever radical separable at the time of the coupling of the oxidized product of developing agents with couplers. It may be selected preferably among radicals combined through oxygen, nitrogen or sulfur atom, the radical being selected from the group consisting of:

a. $-OCOR_5$

Wherein $R_5$ represents an alkyl, phenyl or terpenyl radical.

b. $-O-R_6$

Wherein $R_6$ represents phenyl or a heterocyclic radical.

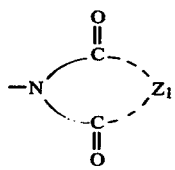

c.

Wherein $Z_1$ represents a non-metal atom group required for the formation of a 5 or 6 membered cyclic ring with

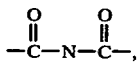

d.

Wherein $Z_2$ represents a non-metal atomic group required for the formation of a 5 or 6 membered cyclic ring with

e.

Wherein $Z_3$ represents a non-metal atom group required for the formation of an imidazol ring, triazol ring, or tetrazol ring together with

and

f.

Wherein $Z_4$ represents a non-metal atom group required for the formation of an aromatic ring or a 5 or 6 membered ring heterocyclic ring together with

containing a nitrogen, oxygen or sulfur atom.

Particularly preferred couplers of the present invention may be represented by Formula III

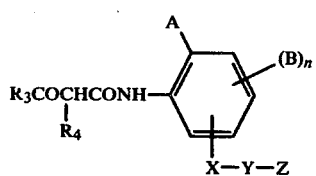

III wherein $R_3$ and $R_4$ represent the same radicals as those of the $R_3$ and $R_4$ in Formula II, X, Y and Z are the same radicals as those of the X, Y and Z in Formula I, and A and $(B)_n$ represent the same meanings as those of the A and $(B)_n$ in Formula II.

Typical examples of the active-site substituents represented by the $R_4$ in Formulas II and III are shown below:

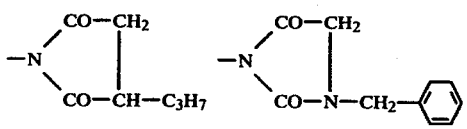

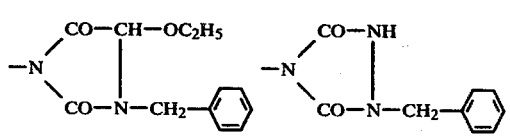

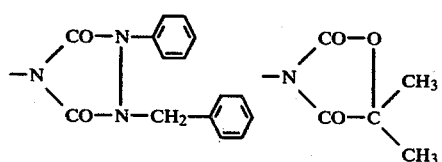

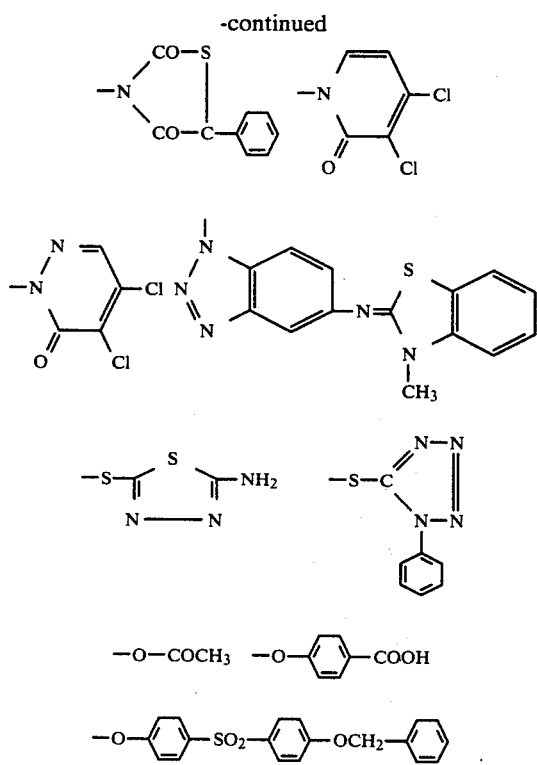

Typical examples of the combining radicals represented by the —X—Y— in the same formula are as follows:

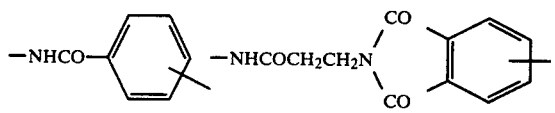

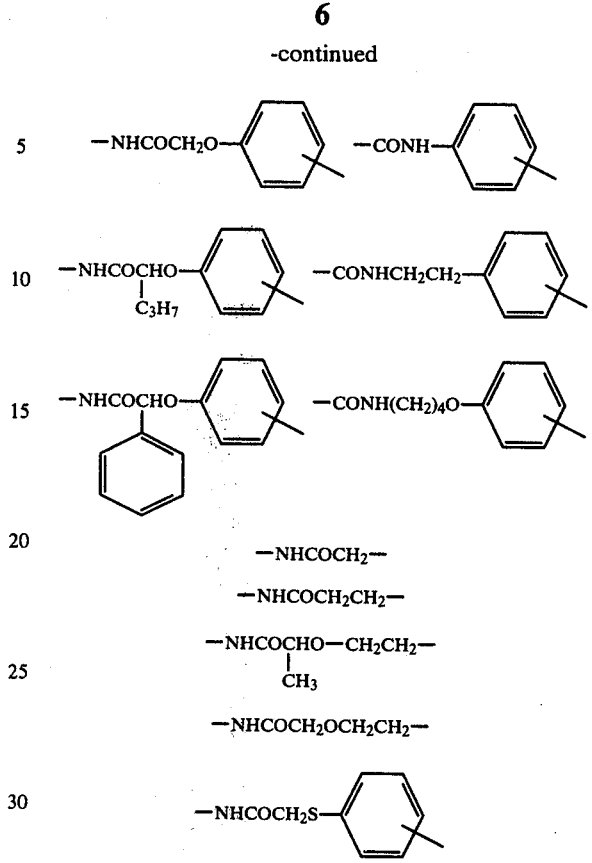

The couplers of the present invention include four-equivalent couplers, two-equivalent couplers and also include such couplers as the development inhibitor-releasing coupler (DIR coupler), and the diffusive dye releasing coupler (DDR coupler).

The following are typical examples of the couplers of the present invention.

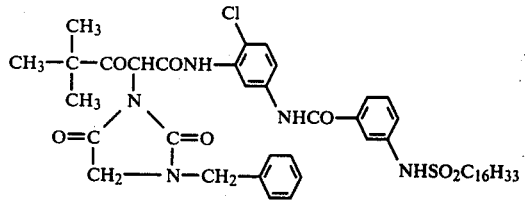

1.

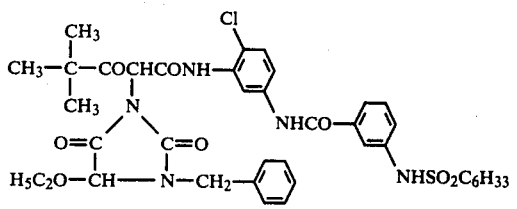

2.

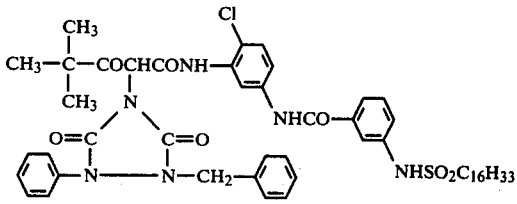

3.

4.
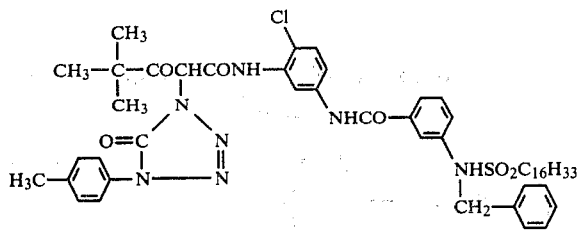
5.
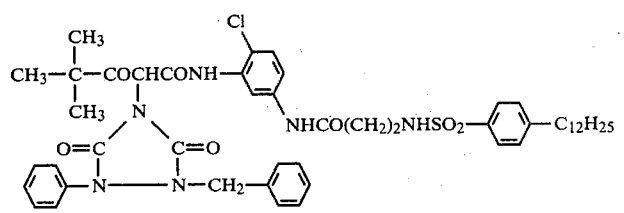
6.
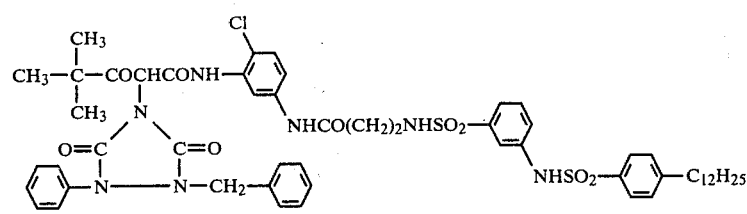
7.
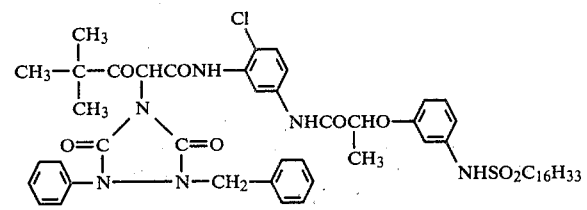
8.
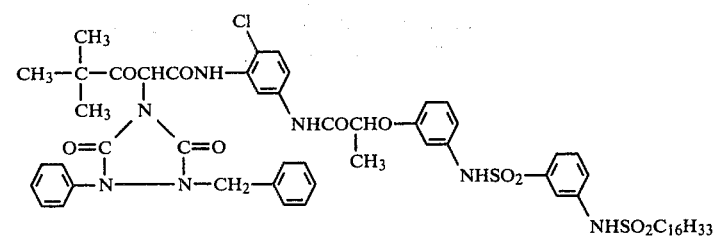
9.
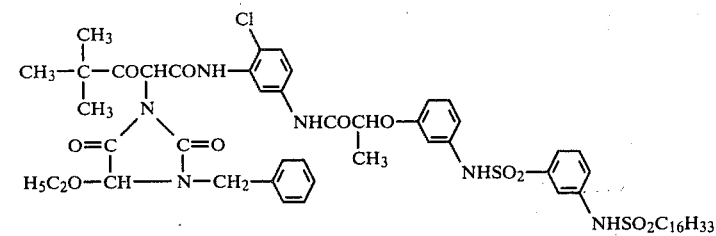
10.
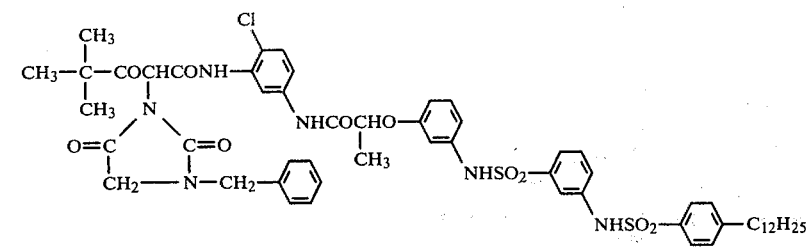

-continued
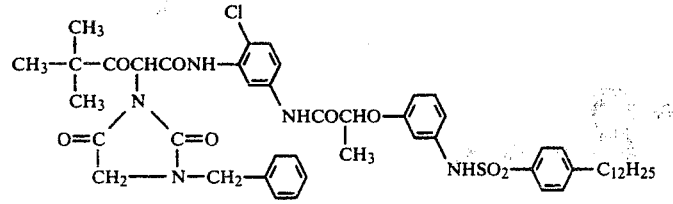
11.
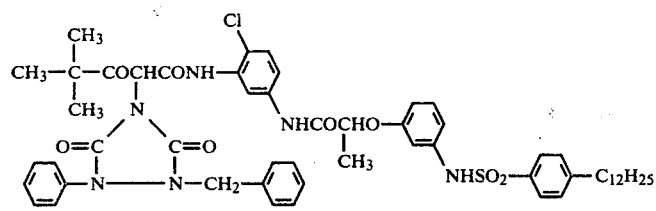
12.
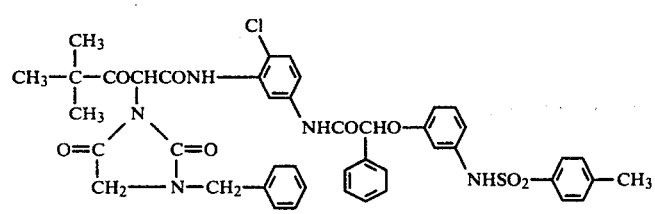
13.
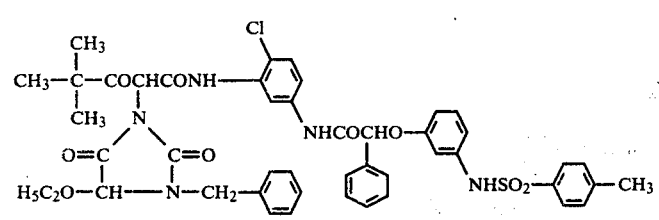
14.
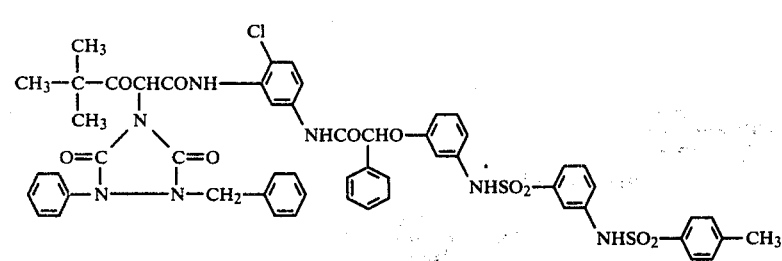
15.
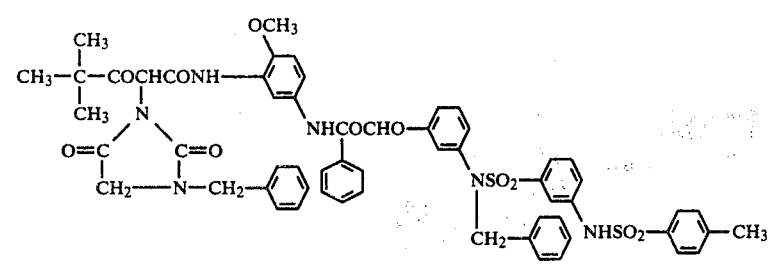
16.
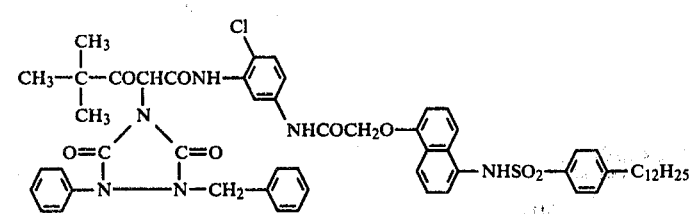
17.

-continued
18.
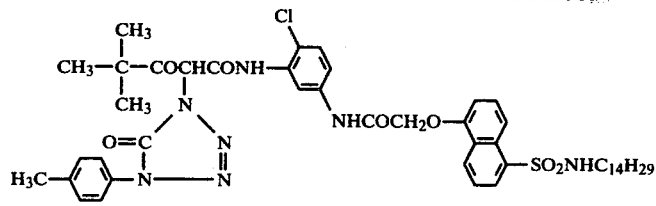
19.
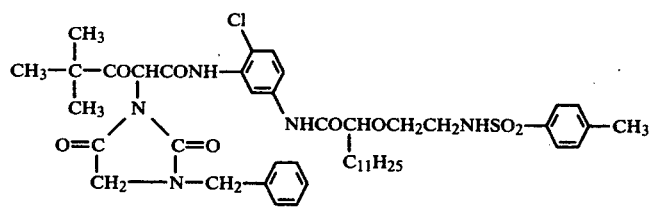
20.
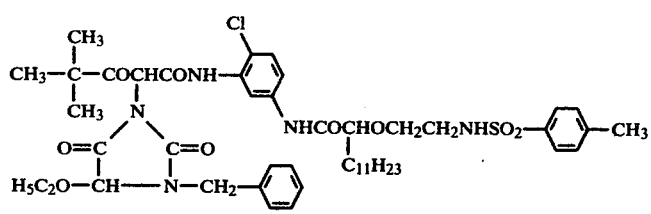
21.
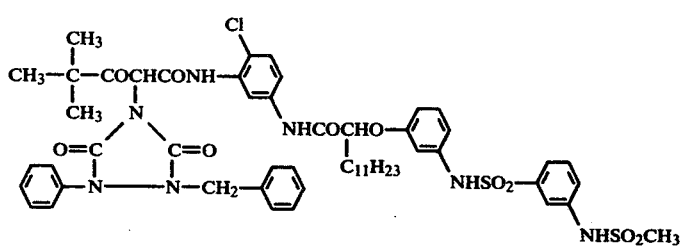
22.
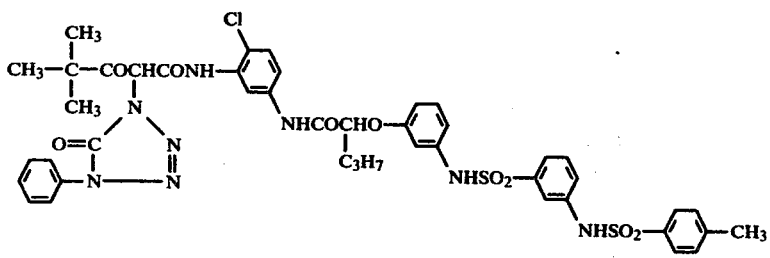
23.
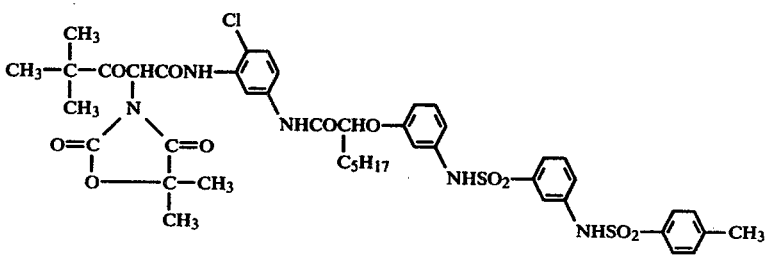
24.
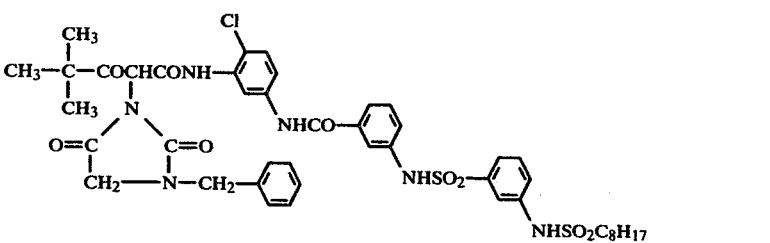

25.
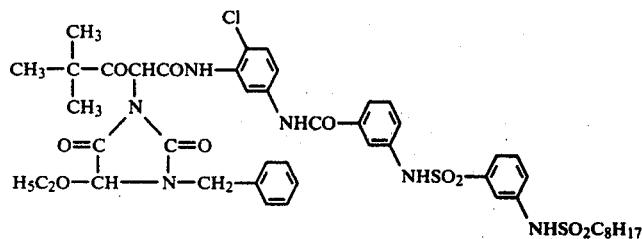
26.
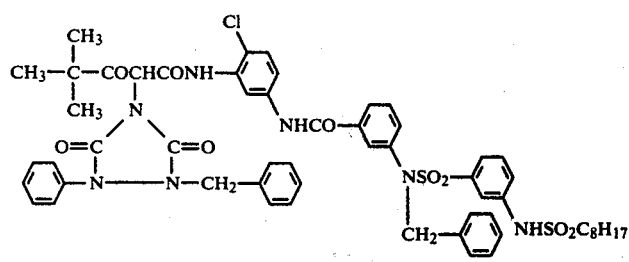
27.
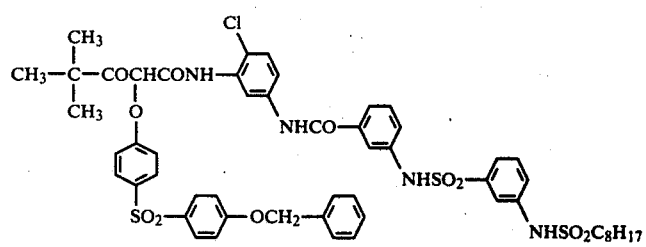
28.
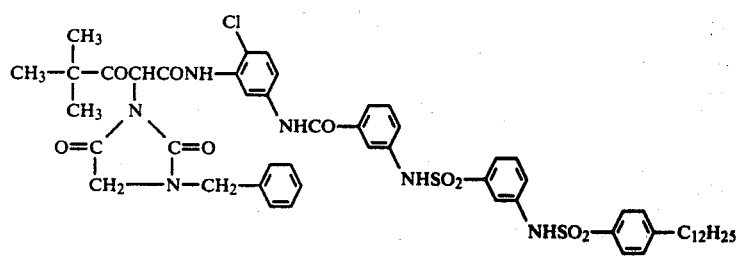
29.
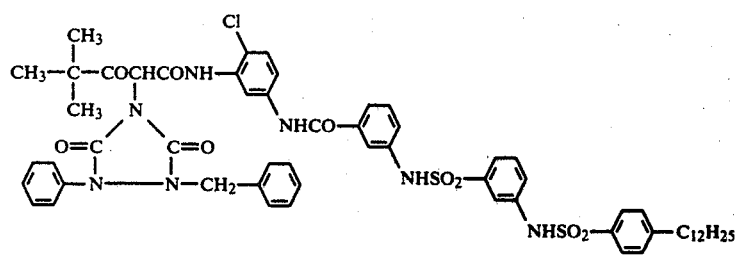
30.
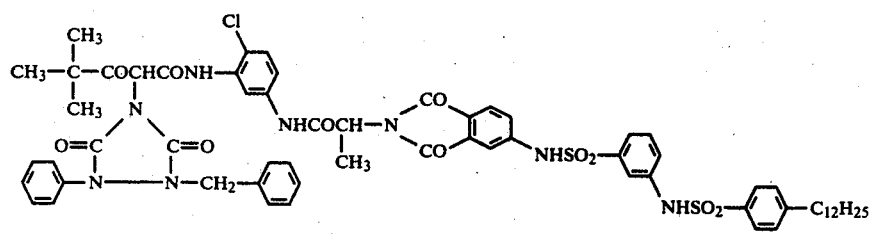

-continued
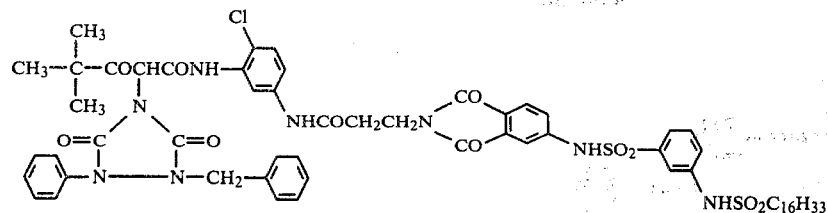
31.
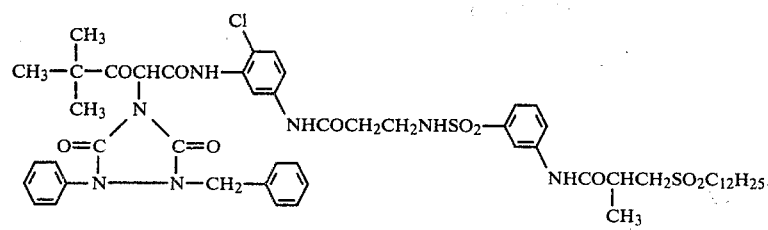
32.
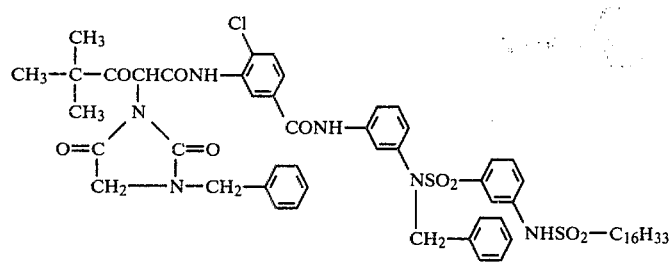
33.
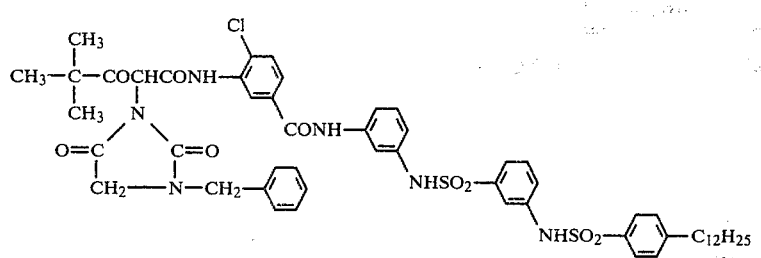
34.
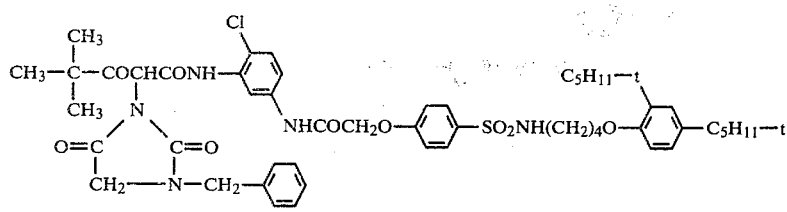
35.
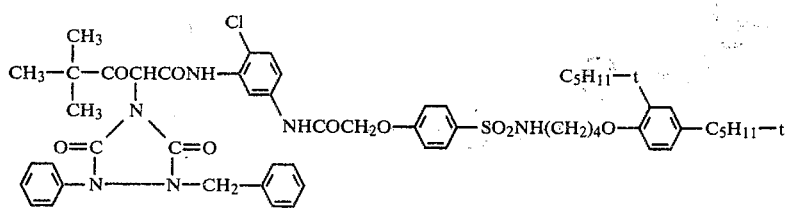
36.
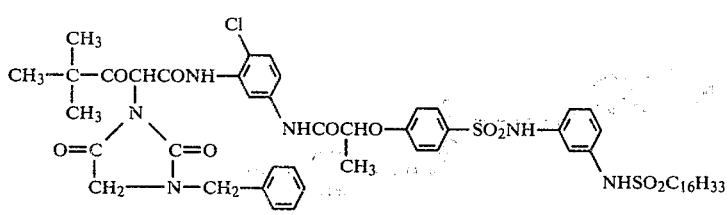
37.

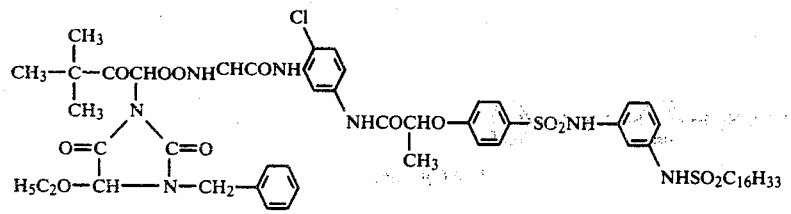
38.
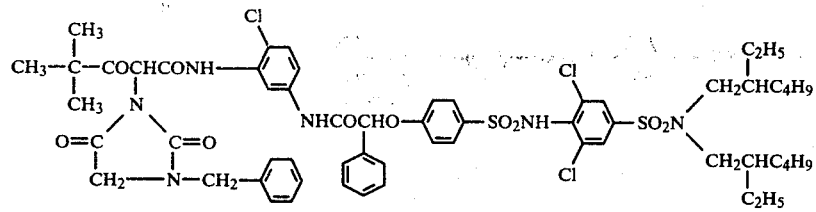
39.
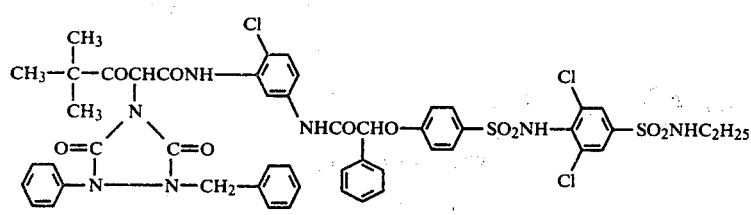
40.
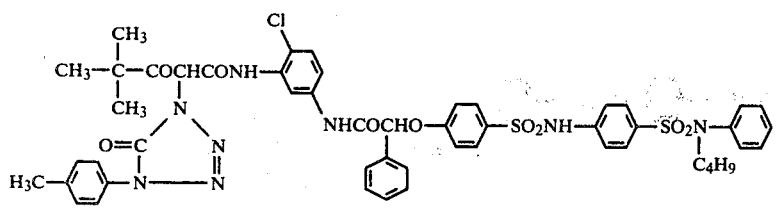
41.
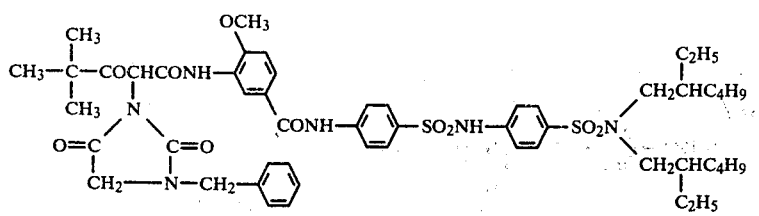
42.
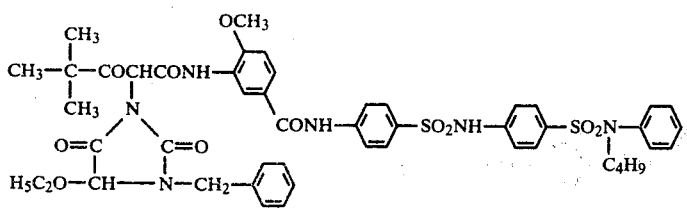
43.
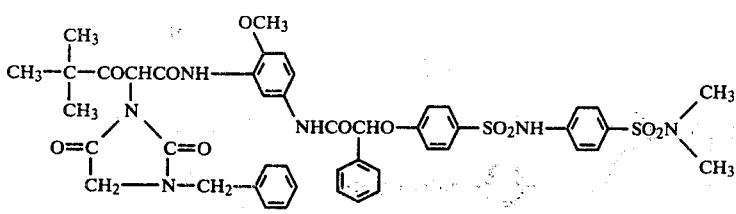
44.

-continued
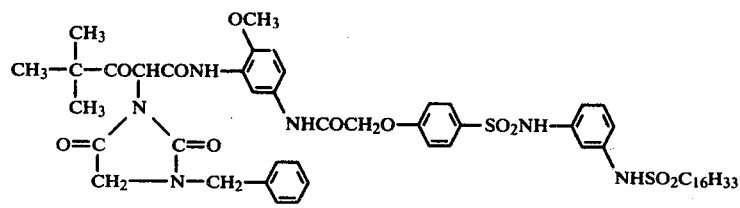
45.
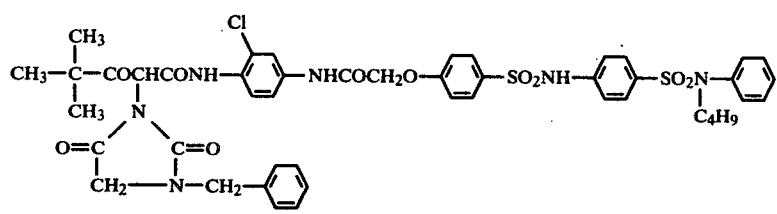
46.
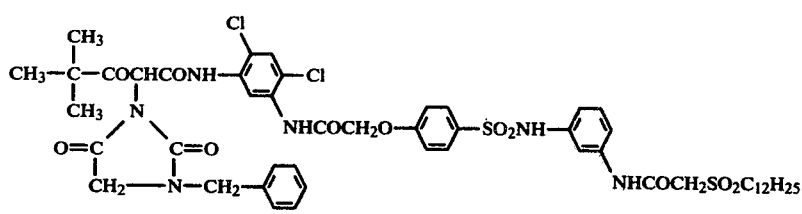
47.
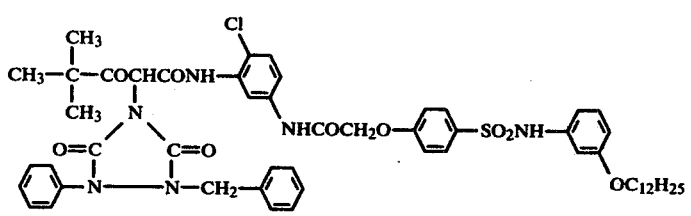
48.
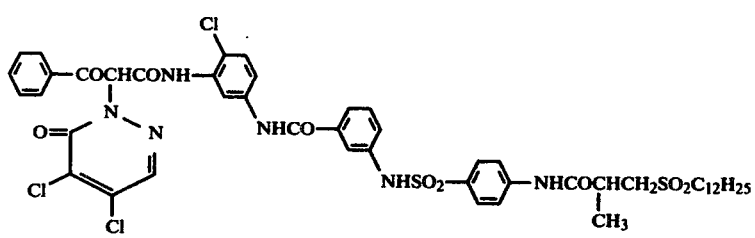
49.
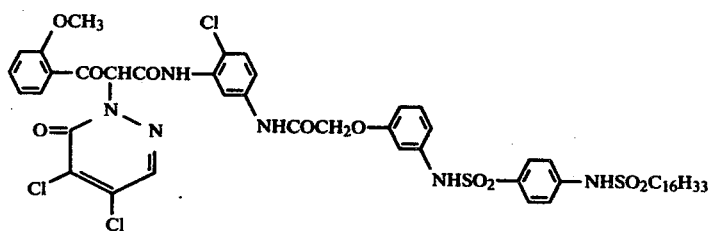
50.
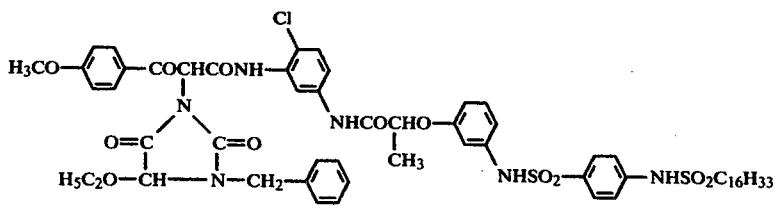
51.

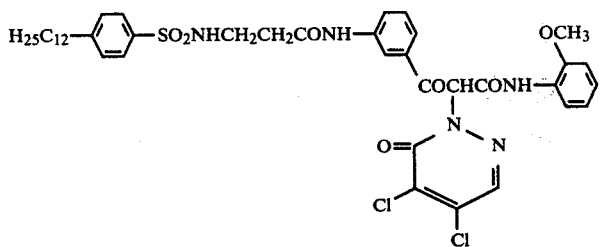
52.
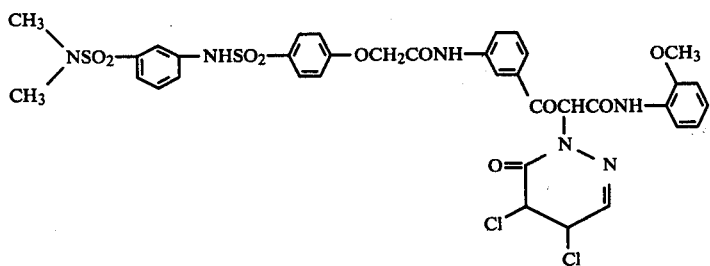
53.
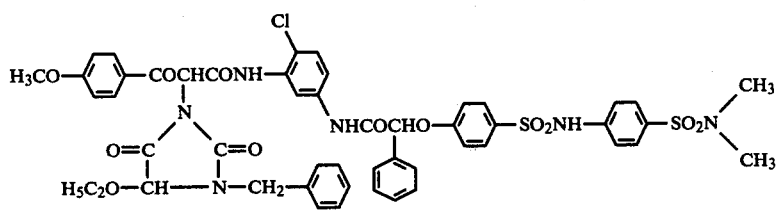
54.
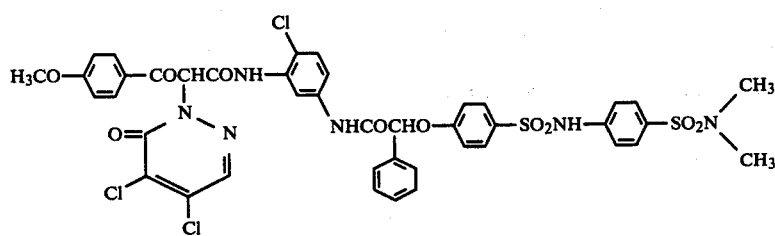
55.
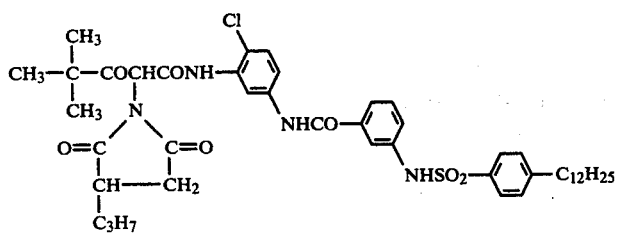
56.
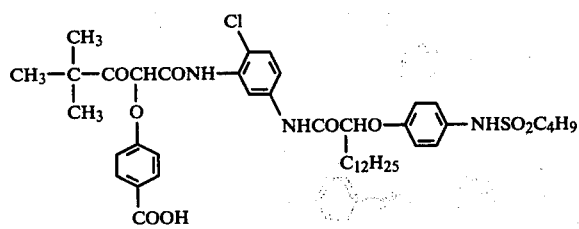
57.

-continued
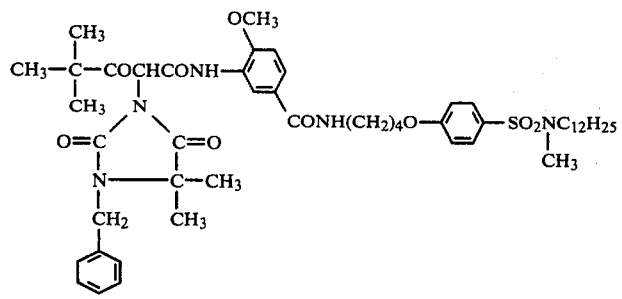 58.
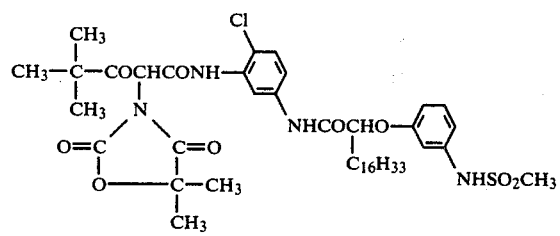 59.
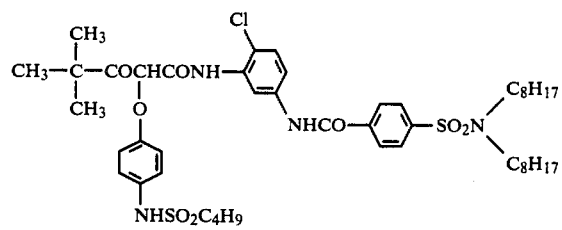 60.
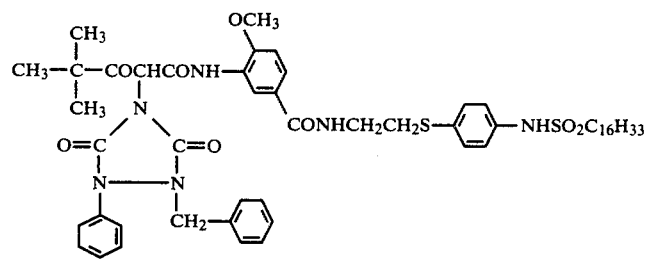 61.
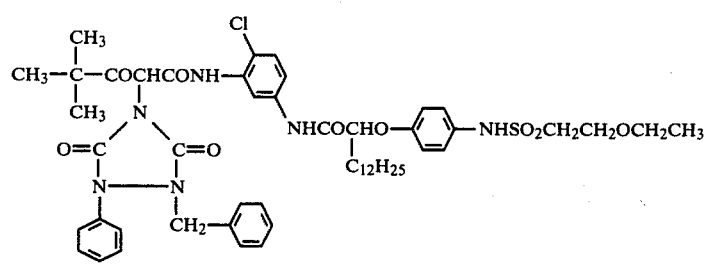 62.
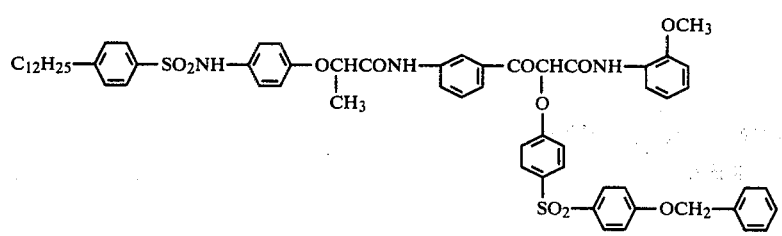 63.

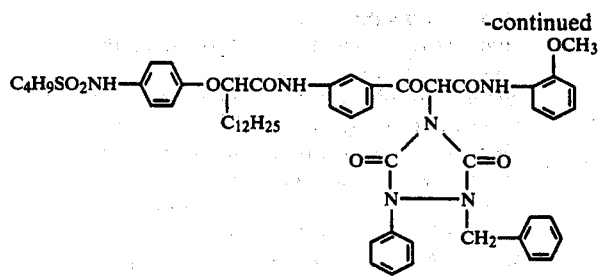

64.

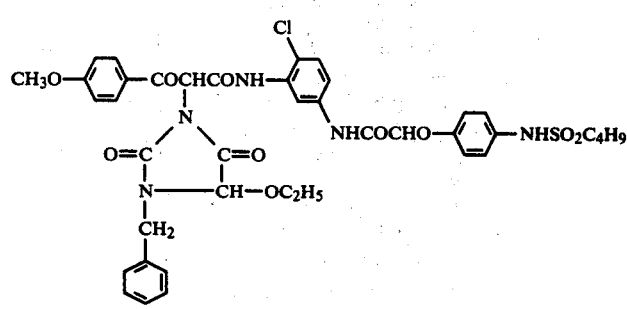

65.

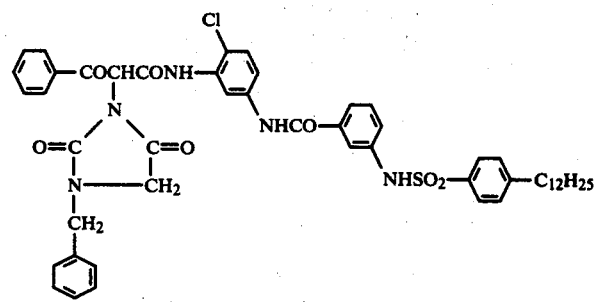

66.

Procedures for synthesizing the couplers used in the present invention are described below with reference to synthesis examples:

SYNTHESIS EXAMPLE 1

(Synthesis of exemplified coupler 1)

520 g of 2-chlor-5-nitroaniline are dissolved in xylene, and to the solution, while refluxing with heating and stirring, is added dropwise 517 g of pivaloylethyl acetate. After completion of the addition the refluxing is further continued for 20 hours, and then the xylene is removed. To the resulting light brown transparent liquid is added n-hexane with heating thereby to gradually deposit white crystals, which are then filtered and dried, thus yielding 480 g of α-pivaloyl-2-chlor-5-nitroacetanilide, M.P. 118°–12° C.

The resulting intermediate product is dissolved in chloroform, and to the solution, while stirring at a temperature of from 25° to 35° C., is added dropwise 400 g of sulfuryl chloride. After continuation of the stirring for 4 hours the solvent is removed under reduced pressure to obtain 899 g of light brown transparent viscous liquid, α-pivaloyl-α-chlor-2-chlor-5-nitroaniline.

33.3 g of the resulting viscous liquid is dissolved in ethyl acetate, and to the solution is added 27.4 g of potassium salt of 1-benzylhydantoin and the mixture is refluxed for four hours, then washed by water, further by brine, subsequently dried under reduced pressure, and finally recrystallized to yield 39 g of white powdered α-pivaloyl-α-(1-benzylhydantoin-3-yl)-2-chlor-5-nitroacetanilide, M.P. 155°–157° C. The resulting product is dissolved in alcohol, and the solution is hydrated in the presence of palladium carbon as a catalyst under normal pressure. Upon completion of the reaction the liquid is filtrated to remove the palladium carbon, and the filtrate is then dried for concentration under reduced pressure. The residuum thus produced is recrystallized in methanol to yield 36.6 g of light yellow powdered α-pivaloyl-α-(1-benzylhydantoin-3-yl)-2-chlor-5-aminoacetanilide, M.P. 166°–168° C. This product is dissolved in ethyl acetate, and to the solution are added 14.8 g of m-nitrobenzoyl chloride and 8 g of triethylamine. The mixed solution is refluxed with heating for three hours, washed, and then dehydrated with anhydrous sodium sulfate. The dehydrated product is rehydrated in the presence of Raney nickel under normal pressure, and then filtrated to remove the Raney nickel. The filtrate is dried under normal pressure. The thus resulting α-pivaloyl-α-(1-benzylhydantoin-3-yl)-2-chlor-5-(3-aminobenzamide)acetanilide is dissolved in acetonitrile, and to the mixed solution are added 26 g of hexadecylsulfonyl chloride and 8 g of triethyl amine. The mixed liquid is refluxed with heating for 14 hours and, upon completion of the reaction, is poured into water. The deposited light brown resin-like product is recrystallized in methanol to yield 37.2 g of objective product, M.P. 105°–110° C.

| Elementary analysis (%) | $C_{46}H_{62}O_7Cl_1S_1$ | | 864.53 | | |
|---|---|---|---|---|---|
| | C | H | N | Cl | S |
| Calculated | 63.90 | 7.23 | 8.10 | 4.10 | 3.71 |
| Found | 63.95 | 7.30 | 8.07 | 4.13 | 3.70 |

SYNTHESIS EXAMPLE 2

(Synthesis of exemplified coupler 3)

39.5 g of an objective product with M.P. 109°–113° C. is obtained in the same manner as in Synthesis example 1 with the exception that 1-phenyl-2-benzyl-1,2,4-triazolidine-3,5-dion potassium salt is used in place of the 1-benzylhydantoin potassium salt.

SYNTHESIS EXAMPLE 3

(Synthesis of exemplified coupler 5)

17.8 g of β-alanine is dissolved in a 1 normal solution of sodium hydroxide, and to the solution are added 46 g of p-dodecyl benzenesulfonyl chloride and 200 ml of ethyl ether. The mixed solution is vigorously stirred for eight hours at room temperature. The reacted liquid is acidified by hydrochloric acid to separate therefrom the resulting ether phase, which is then washed and dried to concentrate under reduced pressure. To the resulting residuum are added 60 ml of thionyl chloride and 6 ml of dimethyl formamide, and the mixture is stirred for three hours at room temperature. The solvent is removed from the mixture under reduced pressure to obtain a residuum, which is then dissolved in acetonitrile, to which are added 32 g of α-pivaloyl-α-(1-phenyl-2-benzyl-1,2,4-triazolidine-3,5-dion-4-yl)-2-chlor-5-aminoacetanilide, the intermediate product obtained according to the same procedure as in Synthesis example 2 and 7 g of triethylamine. The resulting mixture is stirred for six hours at room temperature. After completion of the stirring, the reacted solution is poured into water to deposit a resin-like product, which is then recrystallized in a mixed solvent of ethanol with hexane, thereby yielding 43.7 g of an objective product, M.P. 65°–70° C.

| Elementary analysis (%) $C_{49}H_{61}O_7NCl_1S_1$ | | 913.04 | | |
|---|---|---|---|---|
| | C | H | N | Cl | S |
| Calculated | 64.42 | 6.73 | 9.20 | 3.88 | 3.51 |
| Found | 64.38 | 6.80 | 9.09 | 3.76 | 3.41 |

SYNTHESIS EXAMPLE 4

(Synthesis of exemplified coupler 6)

17.8 g of β-alanine is dissolved in a 1 normal solution sodium hydroxide, To the solution are added 29.5 g of m-nitrobenzenesulfonyl chloride and 200 ml of ethyl ether and the mixed solution is vigorously stirred at room temperature. The ether phase separated by acidifying the thus reacted solution with hydrochloric acid is washed by an aqueous sodium carbonate solution, and thereafter is dried to be concentrated under reduced pressure. The residuum obtained is dissolved in alcohol, hydrated in the presence of palladium carbon as a catalyst, and filtered to remove the palladium carbon. The filtrate is dried to be concentrated under reduced pressure. The concentrated residuum is dissolved in acetonitrile, and to the solution are added 10 g of triethylamine and 34.5 g of p-dodecylbenzenesulfonyl chloride. The mixed solution is refluxed with heating for 14 hours. After completion of the reaction, the liquid is poured into water for the deposition of a resin-like product, which is then extracted by ethyl acetate. The extract is washed with an aqueous sodium hydroxide solution, and then dried again to be concentrated. To the resulting residuum are added 110 ml of thionyl chloride and 10 ml of dimethylformamide. The mixture is stirred for eight hours at room temperature, thereafter is filtered to remove the solvent, and is dried to be concentrated under reduced pressure. The residuum is then dissolved in acetonitrile together with 37.4 g of α-pivaloyl-α-(1-phenyl-2-benzyl-1,2,4-triazolidine-3,5-dion-4-yl)-2-chlor-5-(3-aminobenzamide)acetanilide and 7 g of triethylamine, and the mixed solution is refluxed with heating for 14 hours. The reacted solution is poured into water for the deposition of a resin-like product, which is then recrystallized in methanol, thereby to obtain 38.8 g of an objective product, M.P. 73°–78° C.

| Elementary analysis (%) $C_{55}H_{67}N_7O_9ClS_2$ | | 1069.74 | | |
|---|---|---|---|---|
| | C | H | N | Cl | S |
| Calculated | 61.75 | 6.31 | 9.17 | 3.31 | 5.99 |
| Found | 61.66 | 6.15 | 9.08 | 3.24 | 6.06 |

SYNTHESIS EXAMPLE 5

(Synthesis of exemplified coupler 15)

28.3 g of m-aminophenol is dissolved in ethyl acetate together with 16 g of pyridine and 44.4 g of m-nitrobenzenesulfonyl chloride. The mixed solution is refluxed with heating and stirring for six hours. The reacted solution is washed by a 1% aqueous sodium carbonate solution, then by water, and dehydrated by mirabilite. The filtrate is then hydrated in the presence of Raney nickel as a catalyst under normal pressure. After removing the Raney nickel by filtration, to the filtrate are added 16 g of pyridine and 31.4 g of p-toluenesulfonyl chloride. The mixture is stirred and refluxed with heating for 8 hours. After completion of the reaction, the liquid is washed in order by a 1% aqueous sodium carbonate solution, by a 1% aqueous hydrochloric acid solution, and then by water, and is dried to be concentrated under reduced pressure. The resulting residue is dissolved in methanol, and to the solution is added 9 g of potassium hydroxide, and the mixed solution is boiled for 30 minutes. To the reacted liquid is added 73.1 g of α-pivaloyl-α-(1-phenyl-2-benzyl-1,2,4-triazolidine-3,5-dion-4-yl)-2-chlor-5-(α-bromphenylamide acetate)acetanilide with M.P. 136°–138° C., which has been yielded by recrystallizing in methanol the product obtained by the reaction of α-pivaloyl-α-(1-phenyl-2-benzyl-1,2,4-triazolidine-3,5-dion-4-yl)-2-chlor-5-aminoacetanilide the intermediate obtained in the same manner as in the procedure of Synthesis example 2, with α-bromphenyl acetate chloride in ethyl acetate solvent, and the mixed solution is heated with stirring for eight hours. The reacted liquid is poured into water, and acidified by hydrochloric acid. The deposited resin-like product is recrystallized in methanol, thus yielding 55.5 g of an objective product, M.P. 122°–125° C.

| Elementary analysis (%) $C_{55}H_{50}O_{10}N_7S_2Cl_1$ | | 1068.6 | | |
|---|---|---|---|---|
| | C | H | N | Cl | S |
| Calculated | 61.81 | 4.72 | 9.18 | 3.32 | 6.00 |
| Found | 61.80 | 4.61 | 9.05 | 3.16 | 5.84 |

SYNTHESIS EXAMPLE 6

(Synthesis of exemplified coupler 28)

15.5 g of m-nitrobenzenesulfonyl chloride and 6 g of pyridine are added to a solution of α-pivaloyl-α-(1-benzylhydantoin-3-yl)-2-chlor-5-(3-aminobenzamide) acetanilide dissolved in ethyl acetate, and the mixed solution is heated with stirring for eight hours. The reacted solution is washed by a 1% aqueous sodium carbonate solution and by water, and then is hydrated in the presence of Raney nickel. After removing the Raney nickel by filtration, to the filtrate are added 6 g of pyridine and 20.7 g of p-dodecylbenzenesulfonyl chloride, and the mixture is stirred with heating for eight hours. The reacted solution is washed by a 1% aqueous sodium carbonate solution, then by water, and dried to be concentrated under reduced pressure. The concentrated residuum is recrystallized in methanol, whereby 31.1 g of an objective product can be yielded, M.P. 98°–100° C.

| Elementary analysis (%) $C_{54}H_{63}O_9N_6S_2Cl_1$ | | | | |
|---|---|---|---|---|
| C | H | N | Cl | S |
| Calculated 62.35 | 6.10 | 8.08 | 3.41 | 6.17 |
| Found 62.30 | 5.96 | 7.87 | 3.12 | 6.01 |

SYNTHESIS EXAMPLE 7

(Synthesis of exemplified coupler 29)

32.7 g of an objective product with M.P. 105°–107° C. is obtained in quite the same manner as in Synthesis example 6 with the use of an ethyl acetate solution of α-pivaloyl-α-(1-phenyl-2-benzyl-1,2,4-triazolidine-3,5-dion-4-yl)-2-chlor-5-(3-aminobenzamide) acetanilide, the intermediate obtained in quite the same manner as in Synthesis example 1 with the exception that 36.6 g of 1-phenyl-2-benzyl-1,2,4-triazolidine-3,5-dion potassium salt is used in place of 1-benzylhydantoin potassium salt.

| Elementary analysis (%) $C_{59}H_{66}O_9N_7S_2Cl_1$ 1116.77 | | | | |
|---|---|---|---|---|
| C | H | N | Cl | S |
| Calculated 63.45 | 5.96 | 8.78 | 3.18 | 5.74 |
| Found 63.33 | 5.87 | 8.75 | 3.07 | 5.62 |

SYNTHESIS EXAMPLE 8

(Synthesis of exemplified coupler 30)

A mixture of 88.8 g of phthalic anhydride, 51.6 g of alanine, and 150 ml of acetic acid is refluxed with heating and stirring for four hours, and after completion of the reaction, is spontaneously filtered while heating. The filtrate is then cooled down by the addition of 450 ml of water to yield 102 g of white needle crystals, M.P. 141°–144° C.

The resulting α-phthalimide propionate is little by little added at a temperature of from 10° to 15° C. to a mixed solution of 470 ml of concentrated sulfuric acid and 80 ml of fuming nitric acid (d=1.50) while stirring. After completion of the stirring for three hours at room temperature, the liquid is poured into crushed ice, and the deposited precipitate is separated by filtration and washed. The resulting product is dissolved in 350 ml of ethanol by heating, and then the solution is cooled down by the addition of 700 ml of water, whereby 74 g of crystals can be obtained, M.P. 133°–135° C.

The thus produced α-(4-nitrophthalimide) propionate is refluxed with heating for three hours together with 100 ml of thionyl chloride and 5 ml of dimethylformamide. After completion of the reflux, the thionyl chloride is removed by filtration, and the remaining residuum is dissolved in acetonitrile. To this solution is added 134 g of α-pivaloyl-α-(1-phenyl-2-benzyl-1,2,4-triazolidine-3,5-dion-4-yl)-2-chlor-5-aminoacetanilide, the intermediate product obtained according to the same procedure as in Synthesis example 2, and the mixture is refluxed with heating for four hours. The reacted liquid is dried to be concentrated under reduced pressure, and the resulting residuum is dissolved in benzene. Subsequently the solution is little by little poured into ligroin with stirring. The deposited precipitate is separated by filtration, and further the same manner is repeated, thereby yielding 90.5 g of a light brown product in the powder form with M.P. 130°–133° C.

The thus yielded α-pivaloyl-α-(1-phenyl-2-benzyl-1,2,4-triazolidine-3-dion-4-yl)-2-chlor-5-[α-(4-nitrophthalimide)propionamide] acetanilide is dissolved in 2 liters of tetrahydrofuran, and the solution is hydrated in the presence of Raney nickel as a catalyst under the normal pressure, and thereafter is filtered to remove the Raney nickel. The filtrate is then dried to be concentrated under reduced pressure. The resulting residuum is boiled together with n-hexane thereby to produce 78 g of a white, crystalline α-pivaloyl-α-(1-phenyl-2-benzyl-1,2,4-triazolidine-3,5-dion-4-yl)-2-chlor-5-[α-(4-aminophthalimide)propionamide] acetanilide, M.P. 152°–154° C. The resulting product is dissolved in acetonitrile, and to the solution are added 27.7 g of m-nitrobenzenesulfonyl chloride and 10 g of pyridine. The mixed solution is refluxed with heating for 16 hours. The reacted liquid is poured into water and then extracted by adding ethyl acetate. The extract is washed by a 1% aqueous sodium carbonate solution, and then by water, and further dehydrated by mirabilite. After removing the mirabilite by filtration, the extract is hydrated in the presence of Raney nickel as a catalyst under normal pressure. The Raney nickel is removed by filtration, and to the filtrate are added 34.5 g of dodecylbenzenesulfonyl chloride and 10 ml of pyridine. Then, the mixture is refluxed with boiling for 16 hours. The reacted liquid is washed by a 1% aqueous sodium carbonate solution, then by water, and dried to be concentrated under reduced pressure. The resulting residuum is boiled together with n-hexane, and the deposited precipitate is dissolved in benzene, and is poured into n-hexane with stirring, whereby the deposited light brown precipitate is separated by filtration to yield 45.7 g of an objective product with M.P. 117°–120° C.

| Elementary analysis (%) $C_{63}H_{69}O_{11}N_8S_2Cl_1$ 1213.83 | | | | |
|---|---|---|---|---|
| C | H | N | Cl | S |
| Calculated 62.33 | 5.73 | 9.23 | 2.92 | 5.28 |
| Found 62.31 | 5.68 | 9.11 | 2.89 | 5.24 |

The couplers of the present invention to be incorporated into silver halide photosensitive materials are preferred to be used generally in the range of about 0.07–0.7 mol, preferably, 0.1–0.4 mol per mol of silver halide, but in the case of using for the purpose of improving the characteristics of other couplers to be used in combination therewith, the couplers of the present invention should be used in the range from about 0.01 to 0.1 mol, preferably, from about 0.03 to 0.07 mol per mol of silver halide.

The couplers of the present invention may be used in various ways according to purposes, showing excellent characteristics in their respective uses.

The silver halide color photosensitive materials of the present invention are usable as, e.g., silver halide photosensitive materials for diffusion transfer process, negative type photosensitive materials for general use, reversal type photosensitive materials for general use, positive type photosensitive materials for general use, direct positive type photosensitive materials, etc.

The silver halides for use in these various types of silver halide photosensitive materials may be any of silver chloride, silver iodide, silver iodobromide, silver chlorobromide, and silver chloroiodobromide.

These silver halides may be manufactured in various manners such as neutral process, ammoniacal process according to types of photosensitive materials. And these silver halides can be chemically sensitized by the single or combined use of active gelatin, sulphur sensitizers such as arylthiocarbamide, thiourea, cystin, etc., selenium sensitizer, reduction sensitizers such as stannous salt, polyamine, etc., noble metal sensitizers such as water-soluble gold salts, ruthenium, rhodium, isodium, etc., said combined use being such as the combined use of a gold sensitizer with sulphur sensitizer, of a gold sensitizer with selenium sensitizer, etc.

Further, these silver halides may be optically sensitized up to a desired wavelength region by the single or combined use of optical sensitizing dye.

As the support for photosensitive materials, there may be used materials in the film form or in the sheet form comprising substrata such as paper, laminated paper (composed of e.g., polyethylene and paper), glass, cellulose acetate, cellulose nitrate, polyester (e.g., polyethylene terephthalate), polycarbonate, polyamide, polystyrene, polyolefin, etc.

Color developer for use in developing the exposed photosensitive material contain color developing agents, aromatic primary amines such as p-phenylenediamine series, particularly, for example, diethyl-p-phenylenediamine hydrochloride, monomethyl-p-phenylenediamine hydrochloride, dimethyl-p-phenylenediamine hydrochloride, 2-amino-5-diethyl aminotoluene hydrochloride, 2-amino-5-(N-ethyl-N-dodecylamino) toluene, N-ethyl-N-$\beta$-methane sulfonamide ethyl-3-methyl-4-aminoaniline sulfate, N-ethyl-N-$\beta$-methane sulfonamide ethyl-4-aminoaniline, 4-N-ethyl-N-$\beta$-hydroxyethylaminoaniline, etc.

The couplers of the present invention react with the oxidized product of color developing agents produced at the time of developing silver halides with such color developing solution to form a dye and also other dyes depending on the kinds of couplers.

In order to remove the silver halides or developed silver from a photosensitive material upon completion of the color development, in general, there may be used a combination of a fixer with a bleacher, or a bleach-fix bath, which is used in combination with other various processing such as washing, stopping, stabilizing, etc. For fixing, there may be used silver halide solvents such as sodium thiosulfate, ammonium thiosulfate, etc., and for bleaching, red prussiate, ammonium salt or sodium salt of ethylenediamine ferric tetraacetate, etc.

The constitution of the present invention is what has been described above, but the couplers capable of reacting with the oxidized product of the aromatic primary amines of the present invention have in their diffusion preventive radicals, the group represented by the aforementioned Formula I, whose bonding results in accelerating dye formation, preventing the occurrence of fogs and color stains, and excellent dispersibility in the layers of photosensitive materials such as photosensitive layers, thus enabling the dispersion in high concentration. And the dyes obtained from the couplers have excellent durabilities against light, heat and moisture, and also have such excellent light absorption characteristics that they do not absorb any undesirable rays of light but have sharp absorption of necessary light. And, in the case of incorporating the couplers of the present invention into silver halide photosensitive materials, the photosensitive layers may be made thinner, resulting in the improvement in color image resolution and sharpness as wel as in light transmissibility toward lower layers in multi-layer photosensitive materials, whereby their photographic speed is improved.

Further, it has the advantage that even when the amount of benzyl alcohol to be incorporated is reduced, the amount of the couplers or of silver in photosensitive layers need not be increased, and therefore each of the photosensitive layers may be reduced in thickness, thus providing silver halide materials suitable for the rapid processing at a high temperature.

The present invention is illustrated in further detail below with reference to examples.

EXAMPLE 1

$1.5 \times 10^{31}$ $^1$ mol (per mol of silver halide) of each of the couplers of the present invention as shown in Table 1 (indicated with the numbers of the foregoing exemplified couplers) and the following control couplers was dissolved with heating in ethyl acetate in an amount twice that equivalent to the respective grams thereof by weight, and to the solution was added 1000 ml of 5% aqueous gelatin solution containing 120 ml of 5% sodium dodecylbenzenesulfonate.

The mixed solution was emulsified for dispersion by the use of a colloid mill. The resulting dispersed liquid was added to a 1000 ml of gelatin silver iodobromide emulsion (6 mol% of silver iodide with 94 mol% of silver bromide), and then the emulsion was coated on a film base, which was then dried thereby to yield each sample of silver halide color photosensitive materials (coated thickness: 6$\mu$, coated amount of silver: 3.5 g/m$^2$). Wedge exposures were made in the ordinary manner on these samples obtained, which were then processed in order in the following steps:

| Processing steps (at 38° C.) | Processing period |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |

The compositions of the processing solutions used in the steps are:

| Color Developing Solution | |
|---|---|
| 4-amino-3-methyl-N—ethyl-N—($\beta$-hydroxyethyl)-aniline sulfate | 4.75 g |
| Sodium sulfite, anhydride | 4.25 g |
| Hydroxyamine ½ sulfate | 2.0 g |
| Potassium carbonate, anhydride | 37.5 g |
| Sodium bromide | 1.3 g |
| Trisodium nitrilotriacetate, monohydrated | 2.5 g |
| Potassium hydroxide | 1.0 g |
| Water to make 1 liter, whose pH is controlled 10 by the | |

-continued

| addition of potassium hydroxide thereto | |
|---|---|
| Bleaching Solution | |
| Ethylenediamine ammonium ferric tetraacetate | 100.0 g |
| Ethylenediamine diammonium tetraacetate | 10.0 g |
| Ammonium bromide | 150.0 g |
| Glacial acetic acid | 10.0 ml |
| Water to make 1 liter, whose pH is then controlled 6.0 by adding aqueous ammonia thereto | |
| Fixing Solution | |
| Ammonium thiosulfate (50% aqueous solution) | 162.0 ml |
| Sodium sulfite, anhydride | 12.4 g |
| Water to make 1 liter, whose pH is then controlled 6.5 by adding acetic acid thereto | |
| Stabilizing Solution | |
| Formalin (50% aqueous solution) | 5.0 ml |
| Koniducks (manufactured by Konishiroku Photo Ind. Co., Ltd.) | 7.5 ml |
| Water to make | 1 liter |

Each of the samples was treated in the above baths. The results obtained by measuring the densities of the resulting images with densitometer PD-7R are shown in Table 1.

And, in order to examine the durabilities against light and humidity of the obtained images, the samples were exposed for 100 hours to the light of a xenon fade-o-meter, and afterward placed in an incubator having the condition of 60° C. with 80% relative humidity. The density measured, after two weeks of the above tests, on the point of the initial density 1.0 of each sample was regarded as dye residual rate, whereby the stabilization of each of the couplers was examined.

As seen from Table 1, samples 6-15 containing the yellow couplers having lipophilic constituents of the present invention are markedly excellent in the color developability as compared to samples 1 and 2 containing control yellow couplers (A) and (B) having alkylamide type lipophilic constituents, and also are very excellent in the image preservability as compared to samples 3-5 containing control yellow couplers (C) and (D) having sulfonamide type lipophilic constituents and control yellow coupler (E) having a sulfamoyl type lipophilic constituent respectively.

In addition, the sensitivities indicated in the table are relative sensitivities to that of sample 1 regarded as 100.

TABLE 1

| Sample No. | Exemplified coupler No. | | Sensi- tivity | Fog | Max. density | Durability against | |
|---|---|---|---|---|---|---|---|
| | | | | | | light (%) | humidity (%) |
| 1 | Control | (A) | 100 | 0.14 | 2.18 | 71 | 85 |
| 2 | " | (B) | 115 | 0.14 | 2.21 | 80 | 100 |
| 3 | " | (C) | 143 | 0.17 | 2.56 | 33 | 71 |
| 4 | " | (D) | 150 | 0.17 | 2.67 | 40 | 77 |
| 5 | " | (E) | 148 | 0.17 | 2.60 | 35 | 75 |
| 6 | | 1 | 143 | 0.16 | 2.56 | 80 | 98 |
| 7 | | 3 | 145 | 0.16 | 2.64 | 79 | 97 |
| 8 | | 6 | 148 | 0.17 | 2.67 | 80 | 97 |
| 9 | | 10 | 148 | 0.17 | 2.66 | 80 | 97 |
| 10 | | 15 | 147 | 0.17 | 2.67 | 79 | 97 |
| 11 | | 28 | 146 | 0.17 | 2.65 | 80 | 98 |
| 12 | | 29 | 148 | 0.17 | 2.66 | 78 | 97 |
| 13 | | 30 | 149 | 0.17 | 2.66 | 79 | 97 |
| 14 | | 39 | 148 | 0.17 | 2.65 | 77 | 97 |
| 15 | | 42 | 148 | 0.17 | 2.66 | 77 | 96 |

Control couplers

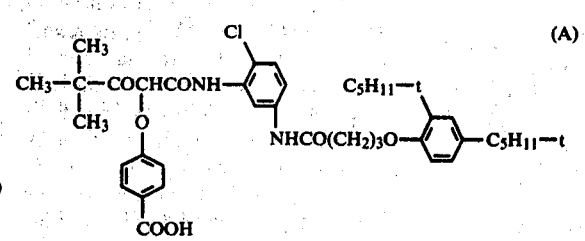

(A) The coupler of the same kind as what is described in British Patent 1077874.

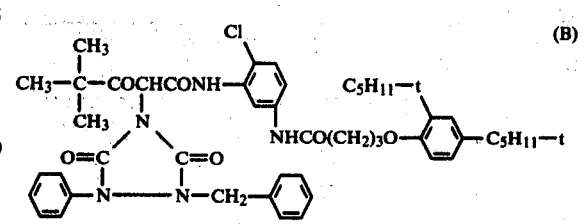

(B) The coupler of the same kind as what is described in Japanese Kokai Patent 48-66834.

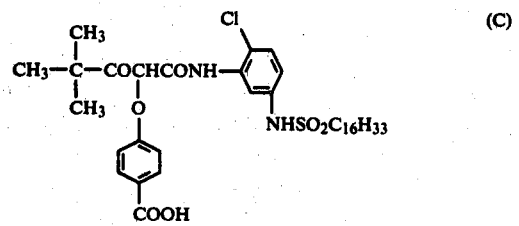

(C) The coupler of the same kind as what is described in Japanese Kokai Patent 50-87650.

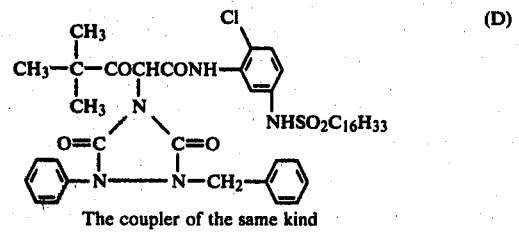

(D) The coupler of the same kind as what is described in Japanese Kokai Patent 52-115219.

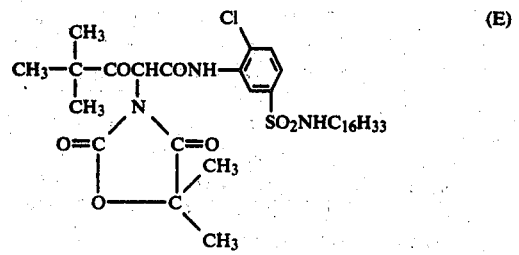

(E) The same as the above.

EXAMPLE 2

Spectral absorption curves of the color images obtained in the same condition as in Example 1 were measured using a spectrophotometer (manufactured by the Hitachi, Ltd.) to examine the maximum absorption wavelength and the absorption density of each of the obtained images on the wavelength of 500 nm at the portion of density 1.0 to the maximum absorption wavelength.

As apparent from Table 2, samples 6-15 containing the yellow couplers having the lipophilic constituents of the present invention show almost the same maximum absorption wavelengths and absorption densities at 500 nm as those of samples 1 and 2 containing control yellow couplers (A) and (B) having alkylimide type lipophilic constituents, and are excellent in their less absorptions of the wavelengths in the useless regions than those of samples 3-5 containing the yellow couplers having sulfonamide type and sulfamoyl type lipophilic constituents.

TABLE 2

| Sample No. | Exemplified coupler No. | | Maximum absorption density | Absorption density at 500 nm |
|---|---|---|---|---|
| 1 | Control | (A) | 449 nm | 0.34 |
| 2 | " | (B) | 449 | 0.30 |
| 3 | " | (C) | 453 | 0.44 |
| 4 | " | (D) | 454 | 0.44 |
| 5 | " | (E) | 458 | 0.49 |
| 6 | | 1 | 449 | 0.30 |
| 7 | | 3 | 449 | 0.31 |
| 8 | | 6 | 450 | 0.31 |
| 9 | | 10 | 450 | 0.31 |
| 10 | | 15 | 449 | 0.32 |
| 11 | | 28 | 450 | 0.30 |
| 12 | | 29 | 450 | 0.31 |
| 13 | | 30 | 450 | 0.31 |
| 14 | | 39 | 450 | 0.30 |
| 15 | | 42 | 448 | 0.30 |

EXAMPLE 3

As shown in Table 3, $3.0 \times 10^{-2}$ mol of each of the yellow couplers (shown with the numbers of the foregoing exemplified couplers) of the present invention and the control couplers is dissolved in a mixed solution of dibutyl phthalate in an amount equivalent to one half of the weight of the respective yellow couplers with 40 ml of ethyl acetate, and the mixture was heated to 50° C. to complete the dissolution. Each of the resulting solutions was mixed with 10 ml of 10% aqueous solution of Alkanol-B (alkylnaphthalene sulfonate; manufactured by Du Pont; the same will apply hereinafter) and 200 ml of 5% aqueous gelatin solution, and the mixed solution was put through a colloid mill several times to be emulsified for producing a dispersed liquid. This dispersed liquid was added to 1,000 ml of gelatin silver chlorobromide emulsion. The emulsion was coated on a laminated paper and then dried to produce a sample of silver halide color photosensitive material. The sample was exposed to light through a wedge in the ordinary procedure, and was then processed in accordance with the following steps and prescriptions:

| Color developing | 3 min. 30 sec. |
|---|---|
| Bleach-fixing | 1 min. 30 sec. |
| Washing | 2 min. |
| Stabilizing | 1 min. |

| Color Developing Solution | |
|---|---|
| Benzyl alcohol | 1.0 ml |
| Sodium hexametaphosphate | 3.00 g |
| Sodium sulfite, anhydride | 1.85 g |
| Sodium bromide | 1.40 g |
| Potassium bromide | 0.50 g |

| -continued | |
|---|---|
| Boric acid ($Na_2B_4O_7 10H_2O$) | 39.10 g |
| N—ethyl-N—[2-(methane sulfonamide ethyl)]-3-methyl-4-aminoaniline sulfate | 4.5 g |
| Water to make 1 liter, whose pH is then controlled 10.3 by adding sodium hydroxide thereto | |
| Bleach-Fix Solution | |
| Ethylenediamine ammonium ferric tetraacetate | 61.0 g |
| Ethylenediamine diammonium tetraacetate | 5.0 g |
| Ammonium thiosulfate | 124.5 g |
| Sodium metabisulfite | 13.3 g |
| Water to make 1 liter, whose pH is then controlled 6.5 | |
| Stabilizing Solution | |
| Glacial acetic acid, trihydrated | 20 ml |
| 800 ml of pure water is added, pH is controlled 3.5-4.0, and is then watered to make 1 liter | |

To examine the durability against light of the dye image obtained by processing in the above baths, the sample was exposed for 100 hours to the light of a xenon fade-o-meter. The density after the exposure measured on the point of the initial density 1.0 was regarded as dye residual rate, whereby each of the couplers was examined.

The dye image of the present invention obtained by processing in the above manner, as shown in Table 3, are remarkably excellent in the color developability as well as in the durability against light as compared to the samples containing control couplers (A), (B), (C), (D) and (E).

In addition, the sensitivities are shown as relative sensitivities to that of sample 16 regarded as 100.

TABLE 3

| Sample No. | Exemplified coupler No. | | Sensitivity | Fog | Maximum density | Durability against light (%) |
|---|---|---|---|---|---|---|
| 16 | Control | (A) | 100 | 0.03 | 2.45 | 80 |
| 17 | " | (B) | 102 | 0.03 | 2.50 | 85 |
| 18 | " | (C) | 118 | 0.04 | 2.93 | 31 |
| 19 | " | (D) | 120 | 0.04 | 3.02 | 36 |
| 20 | " | (E) | 119 | 0.04 | 3.00 | 35 |
| 21 | | 3 | 110 | 0.03 | 2.88 | 80 |
| 22 | | 5 | 117 | 0.04 | 2.90 | 81 |
| 23 | | 8 | 118 | 0.04 | 2.92 | 80 |
| 24 | | 9 | 120 | 0.04 | 2.93 | 82 |
| 25 | | 10 | 120 | 0.04 | 2.93 | 85 |
| 26 | | 28 | 120 | 0.04 | 3.00 | 84 |
| 27 | | 34 | 119 | 0.04 | 3.02 | 81 |
| 28 | | 37 | 118 | 0.04 | 2.98 | 80 |
| 29 | | 38 | 118 | 0.04 | 3.00 | 80 |
| 30 | | 39 | 120 | 0.04 | 3.02 | 83 |

What is claimed is:

1. A color photographic material having a silver halide emulsion layer coated on a support in which the silver halide emulsion layer contains an acylacetanilide yellow coupler having at the acyl or anilide portion thereof a moiety represented by the following formula I:

   I wherein X—Y in the formula I is selected from a group consisting of

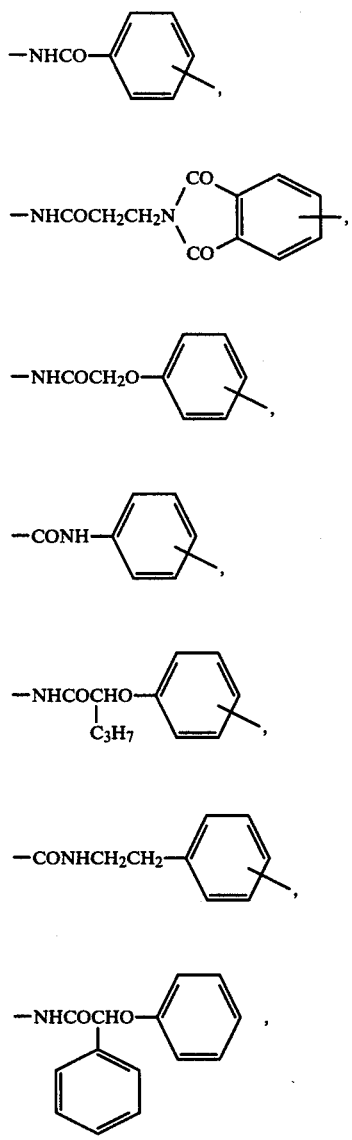

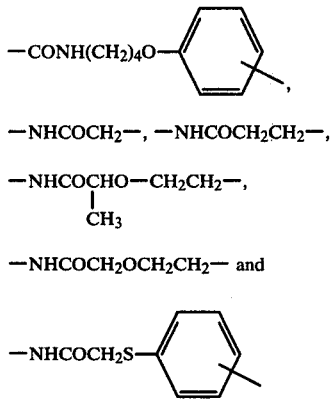

—NHCOCH$_2$—, —NHCOCH$_2$CH$_2$—,

—NHCOCHO—CH$_2$CH$_2$—,
　　　|
　　　CH$_3$

—NHCOCH$_2$OCH$_2$CH$_2$— and

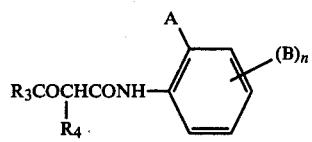

wherein X is —NHCO— or —CONH—, wherein Z is

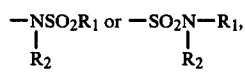

wherein R$_1$ is an alkyl or aryl radical, and R$_2$ is a hydrogen atom or an alkyl or aryl radical, and wherein
a residue of the yellow coupler to which the moiety represented by formula I is attached is represented by the following formula II:

$$\text{R}_3\text{COCHCONH} \underset{\text{R}_4}{|} \text{—} \overset{A}{\underset{}{\bigcirc}} \text{(B)}_n \qquad \text{II}$$

wherein the moiety represented by the formula I is attached to R$_3$ or the benzene ring, R$_3$ represents an alkyl or aryl radical; A represents a halogen atom, an alkyl radical, an alkoxy radical, or an aryloxy radical; B is a halogen atom, an alkyl radical, an alkoxy radical, or an aryloxy radical; n is 0 or 1; R$_4$ is a radical separable at the time of the coupling of the oxidized product of developing agents with couplers.

* * * * *